US010390801B2

(12) United States Patent
Iwama et al.

(10) Patent No.: US 10,390,801 B2
(45) Date of Patent: Aug. 27, 2019

(54) ULTRASONIC DIAGNOSTIC APPARATUS

(71) Applicant: Toshiba Medical Systems Corporation, Otawara-shi (JP)

(72) Inventors: Nobuyuki Iwama, Nasushiobara (JP); Hironobu Hongou, Otawara (JP); Isao Uchiumi, Nasushiobara (JP); Koichi Morikawa, Nasushiobara (JP); Takatoshi Okumura, Yaita (JP)

(73) Assignee: Canon Medical Systems Corporation, Otawara-shi (JP)

( * ) Notice: Subject to any disclaimer, the term of this patent is extended or adjusted under 35 U.S.C. 154(b) by 242 days.

(21) Appl. No.: 14/872,612

(22) Filed: Oct. 1, 2015

(65) Prior Publication Data

US 2016/0095582 A1 Apr. 7, 2016

(30) Foreign Application Priority Data

Oct. 6, 2014 (JP) ................................ 2014-205968

(51) Int. Cl.
*A61B 8/00* (2006.01)
*A61B 8/08* (2006.01)
*A61M 37/00* (2006.01)

(52) U.S. Cl.
CPC .............. *A61B 8/54* (2013.01); *A61B 8/4416* (2013.01); *A61B 8/56* (2013.01); *A61B 8/485* (2013.01); *A61B 8/5246* (2013.01); *A61M 37/0092* (2013.01)

(58) Field of Classification Search
CPC ........................................................ A61B 8/54
See application file for complete search history.

(56) References Cited

U.S. PATENT DOCUMENTS

2004/0047477 A1* 3/2004 Bank ........................ H03F 3/181 381/120
2004/0204744 A1* 10/2004 Penner ................. A61B 5/0031 604/891.1
2010/0331703 A1* 12/2010 Amemiya ................ A61B 8/00 600/459

(Continued)

FOREIGN PATENT DOCUMENTS

JP 2006-101997 A 4/2006
JP 2012-130699 A 7/2012
JP 2014-000260 1/2014

OTHER PUBLICATIONS

Japanese Office Action dated Jun. 19, 2018 in Patent Application No. 2014-205968, 3 Pages.

*Primary Examiner* — Rochelle D Turchen
(74) *Attorney, Agent, or Firm* — Oblon, McClelland, Maier & Neustadt, L.L.P.

(57) ABSTRACT

In general, according to one embodiment, an ultrasonic diagnostic apparatus includes an ultrasonic probe, a plurality of power supplies implemented by circuitry, at least one pulser, and a controller implemented by circuitry. The ultrasonic probe includes a plurality of piezoelectric transducers which generate ultrasonic waves in response to supplied driving signals. The pulser outputs the driving signal based on an applied voltage applied from any one of the plurality of power supplies. The controller switches the plurality of power supplies in accordance with the at least one pulser used for generation of the driving signal in one transmission mode period.

12 Claims, 7 Drawing Sheets

(56) References Cited

U.S. PATENT DOCUMENTS

2013/0096430 A1* 4/2013 Yoshiara .............. A61B 8/0841
600/438
2015/0087990 A1* 3/2015 Honda ................. H03K 17/063
600/459
2015/0227127 A1* 8/2015 Miller .................. G05B 19/042
700/244

* cited by examiner

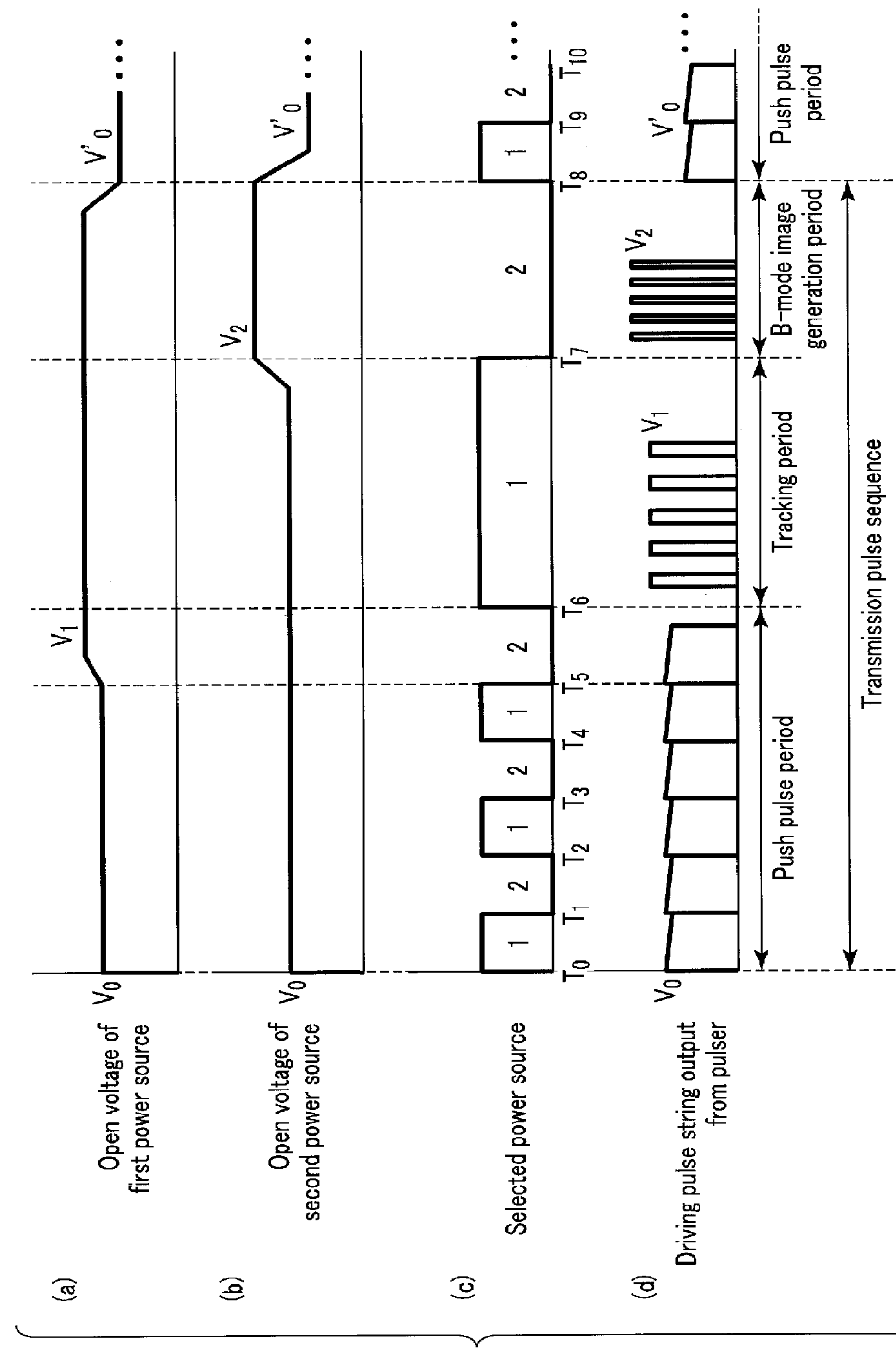
F I G. 3

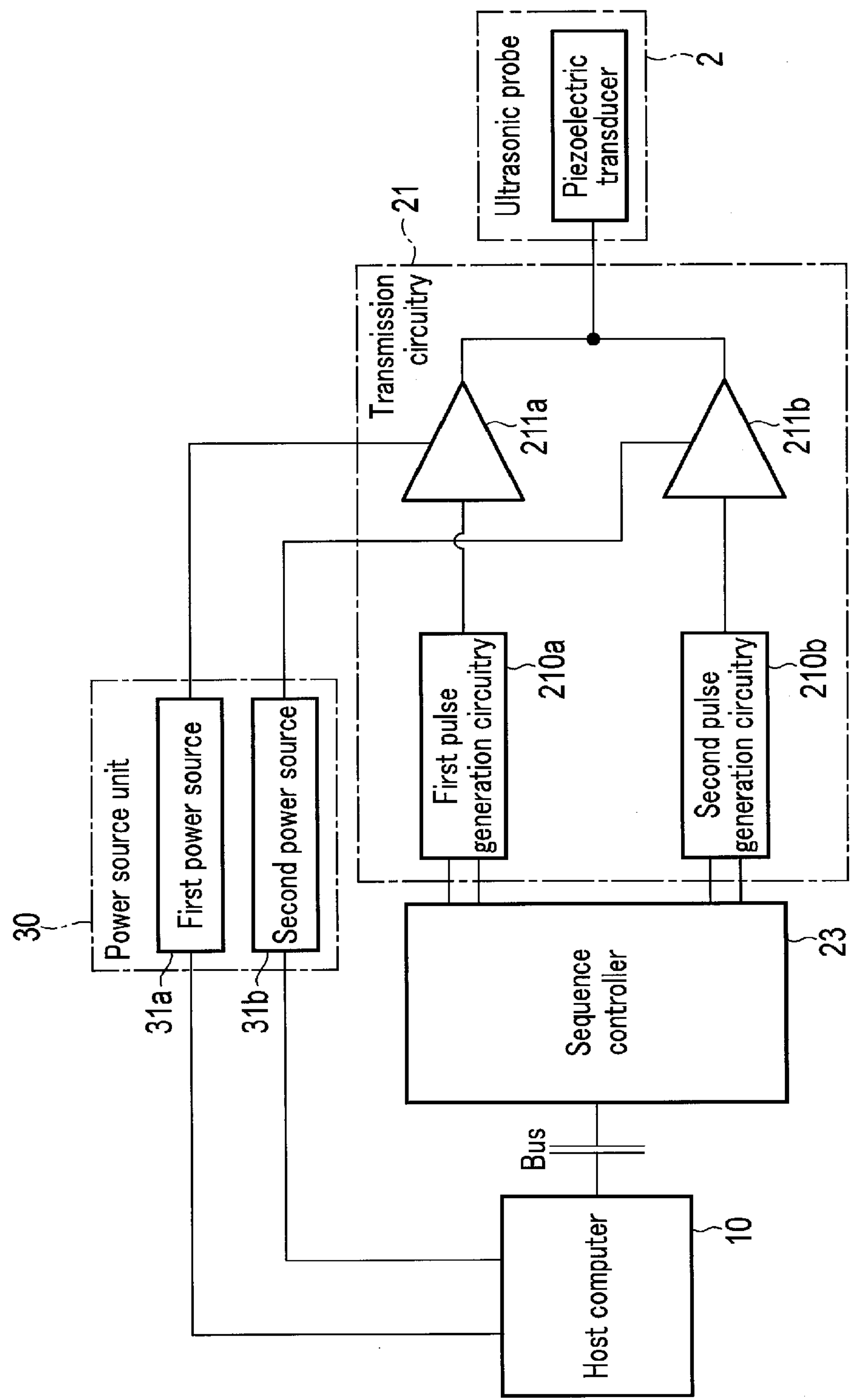
F I G. 5

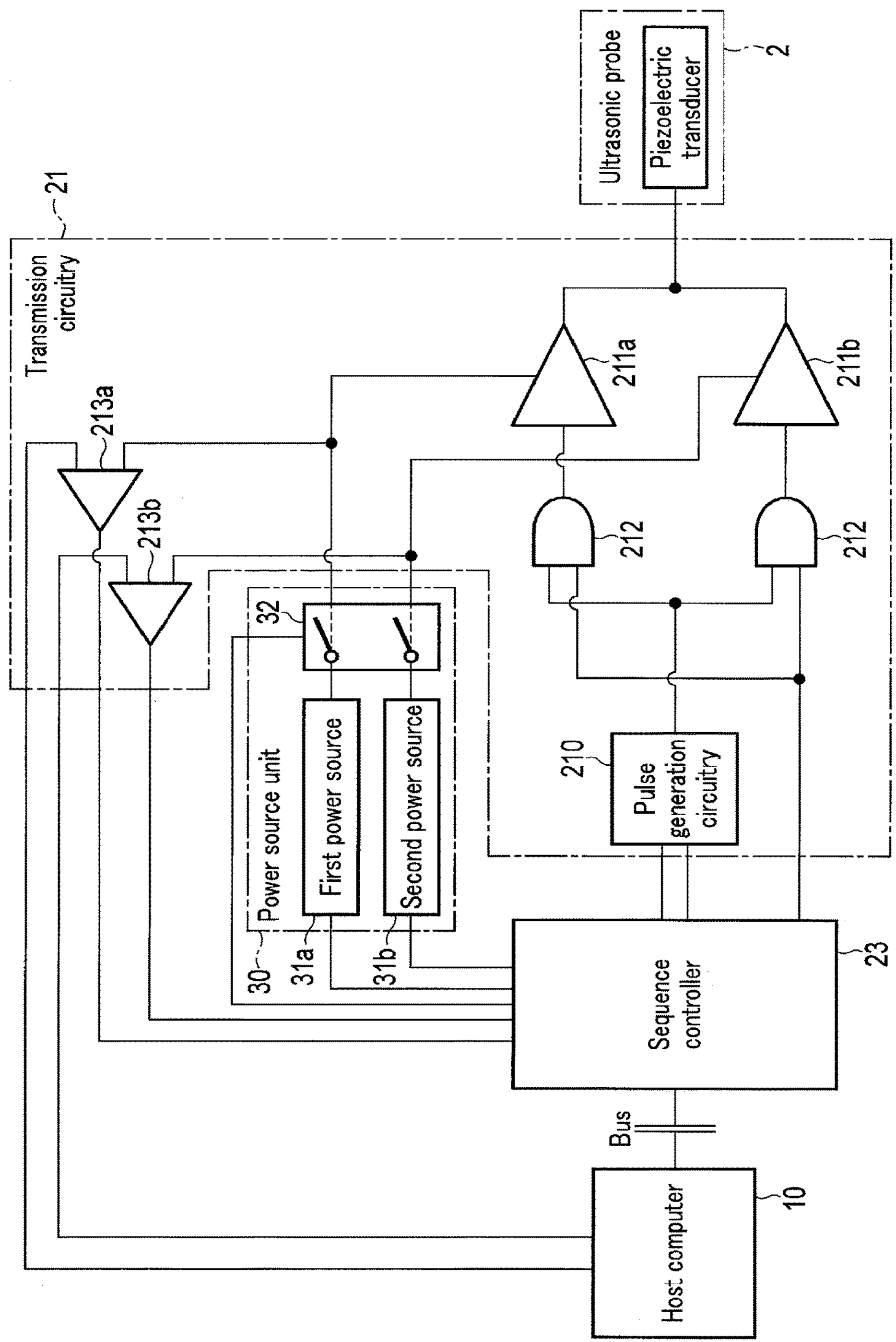
F I G. 7

ULTRASONIC DIAGNOSTIC APPARATUS

CROSS-REFERENCE TO RELATED APPLICATIONS

This application is based upon and claims the benefit of priority from the prior Japanese Patent Application No. 2014-205968, filed Oct. 6, 2014 the entire contents of which are incorporated herein by reference.

FIELD

Embodiments described herein relate generally to an ultrasonic diagnostic apparatus which images a region scanned with ultrasonic waves in an object, and implements, for example, shear wave elastography of diagnosing the hardness of living organs such as the liver, the breasts, and the like, a drug delivery system which quantitatively and spatially controls the internal distribution of the drug administered into an object by irradiation with ultrasonic waves, and the like.

BACKGROUND

In the field of ultrasonic diagnosis, for example, the elastography diagnosis of diagnosing hardness is performed in actual medical practice. Elastography diagnosis is the diagnostic method of diagnosing that a given tissue is harder than a normal region because of hepatic cirrhosis or fibrosis or calcification of the tissue. In general, an examiner irradiates an object with ultrasonic waves while repeatedly pressing and releasing the object by moving an ultrasonic probe with his/her hand. Diagnosis of hardness is performed by analyzing reflected waves from a living tissue. The method of repeating such pressing and releasing action has problems, for example, that measured values vary depending on the way of moving the probe and different examiners obtain different results.

Recently, attention has been paid to a technique called shear wave elastography. First of all, shear waves are generated from a living body by irradiating an object with relatively strong ultrasonic waves (push pulses) from an ultrasonic probe. The propagation velocity of the shear waves is measured with tracking pulses output from the ultrasonic probe. The result is analyzed and visualized. The resultant image is then superimposed on a B-mode image to perform diagnosis of hardness. Unlike general elastography, shear wave elastography needs not repeat pressing and releasing action, and hence can implement measurement with more ease and higher reproducibility.

To generate such push pulses in shear wave elastography, a driving pulse string (driving signal) having a high peak value of 100 V or the like is used. An applied high voltage (for example, 100 V) is required to generate a driving pulse string having a high peak value. If, however, a high voltage is applied to a pulser, a transmission power source lacks in charge (that is, charge accumulated in the capacitor in the transmission power source). This often leads to a droop in applied voltage (a drop in voltage) to the pulser relative to the set voltage (open voltage) of the transmission power source.

On the other hand, in the field of ultrasonic diagnosis, for example, a DDS (Drug Delivery System) is used in actual medical practice. In this system, a drug capsule is administered to an object in advance, and an operator such as a doctor intentionally breaks the drug capsule in the body by irradiating the capsule with relatively strong ultrasonic waves from an ultrasonic probe of an ultrasonic diagnostic apparatus. It is then possible to quantitatively and spatially control the internal distribution of the drug in the object by using the breakage of the capsule. In addition, using an ultrasonic diagnostic apparatus can simultaneously perform diagnosis and the breakage of a drug capsule.

In the use of a drug delivery system, a driving pulse string having a high peak value is used even when such relatively strong ultrasonic waves are applied. To generate a driving pulse string having a high peak value, an applied high voltage (for example, 100 V) is required. For this reason, like the above shear wave elastography, the above technique has often the problem of the occurrence of voltage droops.

BRIEF DESCRIPTION OF THE DRAWING

FIG. 3 represents an example of timing charts representing an ultrasonic transmission/reception sequence using a power switching function in shear wave elastography according to the first embodiment;

FIG. 5 is a block diagram representing an example of transmission circuitry in a conventional ultrasonic diagnostic apparatus;

FIG. 7 is a block diagram representing an example of transmission circuitry according to the second embodiment.

DETAILED DESCRIPTION

Figure 1:
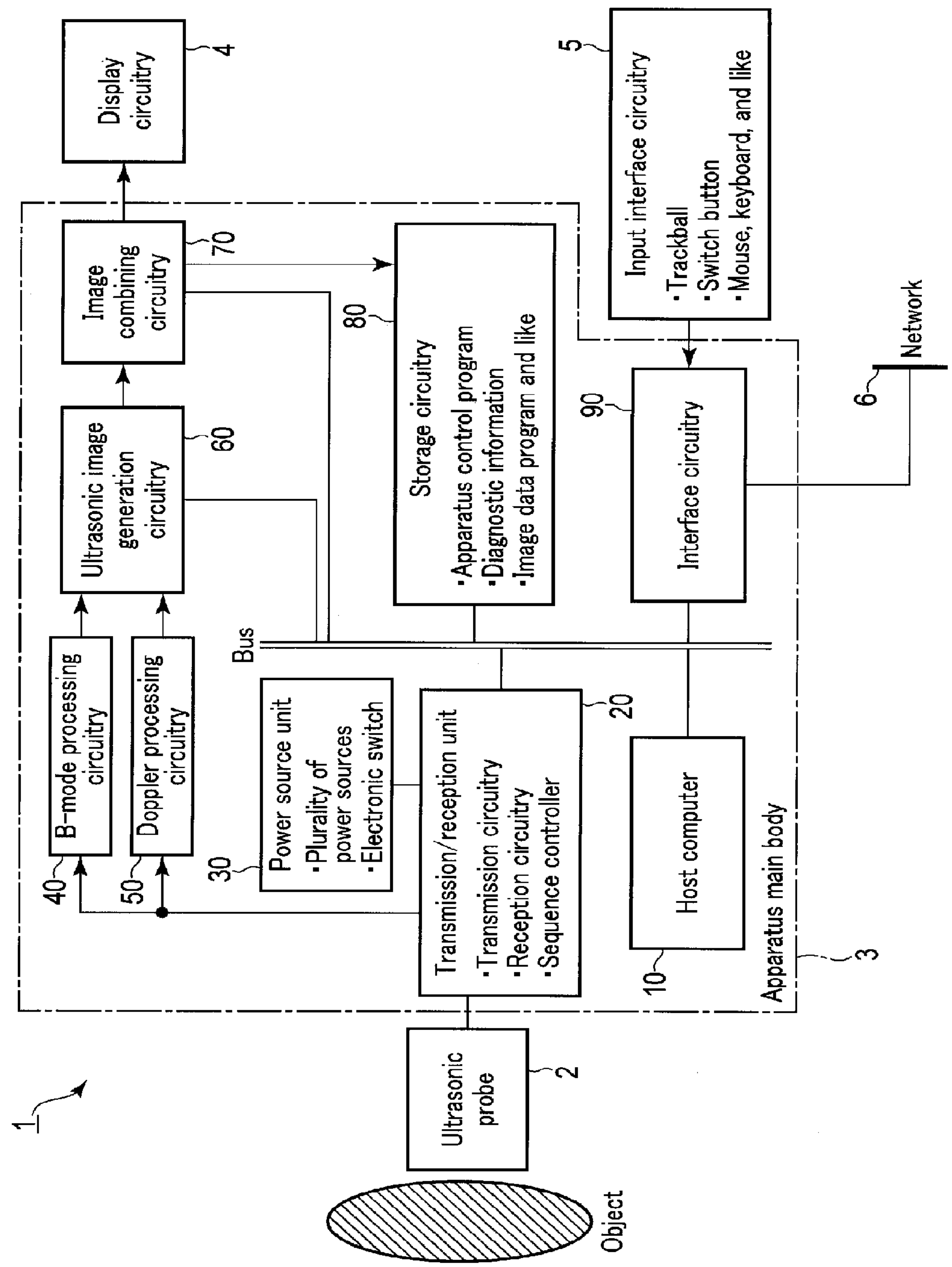
FIG. 1 is a block diagram representing an example of the arrangement of an ultrasonic diagnostic apparatus according to the first embodiment.

In general, according to one embodiment, an ultrasonic diagnostic apparatus includes an ultrasonic probe, a plurality of power supplies implemented by circuitry, at least one pulser, and a controller implemented by circuitry. The ultrasonic probe includes a plurality of piezoelectric transducers which generate ultrasonic waves in response to supplied driving signals. The pulser outputs the driving signal based on an applied voltage applied from any one of the plurality of power supplies. The controller switches the plurality of power supplies in accordance with the at least one pulser used for generation of the driving signal in one transmission mode period.

The embodiments will be described below with reference to the accompanying drawing. The same reference numerals in the following description denote the same constituent elements having almost the same arrangements, and a repetitive description will be omitted.

(First Embodiment)

FIG. 1 represents the arrangement of an ultrasonic diagnostic apparatus 1 according to the first embodiment. The ultrasonic diagnostic apparatus 1 includes an ultrasonic probe 2, an apparatus main body 3, display circuitry 4 (a monitor or display), and input interface circuitry 5. In addition, a network 6 capable of external communication may be connected to the ultrasonic diagnostic apparatus 1 via interface circuitry 90 of the apparatus main body 3.

The ultrasonic probe 2 includes a plurality of piezoelectric transducers, a matching layer, and a backing member provided on the back surface side of the plurality of piezoelectric transducers. The plurality of piezoelectric transducers are acoustoelectric reversible conversion elements such as piezoelectric ceramic elements. The plurality of piezoelectric transducers are arranged in parallel and mounted on the distal end of the ultrasonic probe 2. Each piezoelectric transducer generates an ultrasonic wave in response to the driving pulse string (driving signal) transmitted and supplied from a transmission/reception unit 20 (to be described later).

When an object is irradiated with ultrasonic waves via the ultrasonic probe 2, the ultrasonic waves with which the object are irradiated are reflected by a discontinuity surface of acoustic impedance of a living body tissue in the object. The piezoelectric transducers receive the reflected ultrasonic waves and generate an echo signal. The amplitude of this echo signal depends on an acoustic impedance difference on the discontinuity surface as a boundary concerning the reflection of the ultrasonic waves. Identical piezoelectric transducers may be selectively used as a piezoelectric transducer (for transmission) for the generation of ultrasonic waves and a piezoelectric transducer (for reception) for the generation of echo signals by deciding a transmission timing and a reception timing when, for example, irradiating an object with discrete ultrasonic waves (pulse waves). Alternatively, for example, when irradiating an object with a continuous ultrasonic wave (continuous wave), this apparatus may separately include piezoelectric transducers for transmission and piezoelectric transducers for reception. The frequency of the echo signal generated when transmission ultrasonic waves are reflected by a moving blood flow, the surface of the cardiac wall, or the like is subjected to a frequency shift depending on the velocity component of the moving body (the blood flow and the surface of the cardiac wall) in the ultrasonic transmission direction due to the Doppler effect.

The apparatus main body 3 includes a host computer 10, a transmission/reception unit 20, a power source unit 30, B-mode processing circuitry 40, Doppler processing circuitry 50, ultrasonic image generation circuitry 60, image combining circuitry 70, storage circuitry 80 (a memory), and interface circuitry 90.

The host computer 10 includes a processor such as a CPU (Central Processing Unit) and is mainly in charge of controlling the overall operation of the ultrasonic diagnostic apparatus 1. Note that a specific operation of the host computer 10 will be described later in association with a description of other portions.

The transmission/reception unit 20 includes transmission circuitry and a sequence controller (implemented by circuitry). The transmission circuitry and the sequence controller are denoted by reference numerals in FIG. 2 and subsequent figures and will be described in detail later. The transmission circuitry transmits driving pulse strings to the respective piezoelectric transducers of the ultrasonic probe 2. The reception circuitry generates a reception signal based on the echo signal generated by each piezoelectric transducer.

Driving pulse strings transmitted to the respective piezoelectric transducers also differ in the respective periods in an ultrasonic transmission/reception sequence (For example, a sequence constituted by three periods, i.e., a push pulse transmission period, a tracking period, and a B-mode image generation period). In these periods, control having a high time resolution (e.g., on the order of several ten μs to several hundred μs) is required. The sequence controller has a higher time resolution than the host computer 10 configured to mainly perform software processing by using CPU, and executes control of a sequence requiring the high time resolution. An operation mode of the ultrasonic diagnostic apparatus 1 which transmits strong ultrasonic waves such as push pulses will be referred to as a transmission mode.

The power source unit 30 includes a plurality of power source circuits (to be simply referred to as power sources hereinafter: note that FIG. 2 (to be described later) exemplarily represents two power sources, i.e., a first power source 31*a* and a second power source 31*b*) and an electronic switch (ON/OFF switching means) which switches between executing and stopping voltage application from the plurality of power sources. Note that a detailed operation will be described again with reference to FIG. 2.

The B-mode processing circuitry 40 includes an envelope detector and a logarithmic converter. The envelope detector executes envelope detection of the reception signal output from the reception circuitry. The envelope detector outputs the envelope-detected signal to the logarithmic converter. The logarithmic converter relatively enhances a weak signal by logarithmically converting the envelope-detected signal. The B-mode processing circuitry 40 generates a signal value for each depth on each scanning line and each ultrasonic transmission/reception based on the signal enhanced by the logarithmic converter. Note that the B-mode processing circuitry 40 may generate volume data instead of a signal value for each depth on each scanning line and each ultrasonic transmission/reception. The data generated by the B-mode processing circuitry 40 will be collectively referred to as B-mode data hereinafter.

The Doppler processing circuitry 50 includes a mixer, an LPF (Low Pass Filter), and a velocity/variance/power computation device. The mixer multiplies the reception signal output from the reception circuitry by a reference signal having a frequency $f_0$ equal to the transmission frequency. This multiplication obtains a signal having a component with a Doppler shift frequency $f_d$ and a signal having a frequency component of $(2f_0+f_d)$. The LPF removes a signal of a high-frequency component $(2f_0+f_d)$ from a signal having two types of frequency components from the mixer. The Doppler processing circuitry 50 generates a Doppler signal having the component with the Doppler shift frequency $f_d$ by removing the signal of the high-frequency component $(2f_0+f_d)$.

Note that the Doppler processing circuitry 50 may use a quadrature detection scheme to generate Doppler signals. In this case, the Doppler processing circuitry 50 performs quadrature detection to convert a reception signal (RF signal) into an IQ signal. The Doppler processing circuitry 50 generates a Doppler signal having the Doppler shift frequency $f_d$ by performing complex Fourier transform of the IQ signal. Doppler signals are, for example, Doppler components based on a blood flow, tissue, and contrast medium. The velocity/variance/power computation device includes an MTI (Moving Target Indicator) filter, an LPF filter, and an autocorrelation computation device. Note that this device may include a cross-correlation computation device instead of the autocorrelation computation device. The MTI filter removes a Doppler component (a clutter component) caused by the respiratory movement or pulsatory movement of an organ or the like from a generated Doppler signal. The MTI filter is used to extract a Doppler component concerning a blood flow from a Doppler signal. The LPF is used to extract a Doppler component concerning the movement of the tissue from a Doppler signal.

The ultrasonic image generation circuitry 60 includes a DSC (Digital Scan Converter) and an image memory. The ultrasonic image generation circuitry 60 executes coordinate conversion processing (resampling) for the DSC. Coordinate conversion processing is to convert, for example, a scanning line signal string for ultrasonic scanning, which is formed from B-mode data, Doppler data, and propagation time data, into a scanning line signal string in a general video format typified by a TV format. The ultrasonic image generation circuitry 60 generates an ultrasonic image as a display image by executing coordinate conversion processing. More specifically, the ultrasonic image generation circuitry 60 generates a B-mode image based on B-mode data. The ultrasonic image generation circuitry 60 generates a Doppler image such as an average velocity image, a variance image, or a power image based on Doppler data.

The ultrasonic image generation circuitry 60 generates a shear wave propagation image assigned with a hue in accordance with the propagation time at each position in a predetermined region based on propagation time data and the propagation time hue correspondence table stored in the storage circuitry 80. The propagation time hue correspondence table is a correspondence table of hues corresponding to propagation time values. For example, a hue corresponding to a propagation time of 0 is blue. For example, hues are defined as blue, blue green, green, yellow green, yellow, orange, and red in the order named with an increase in propagation time, with the maximum propagation time corresponding to red.

The image combining circuitry 70 combines character information of various types of parameters, scale marks, and the like with ultrasonic images. The image combining circuitry 70 generates a superimposed image by superimposing a shear wave propagation image on a B-mode image upon alignment.

The storage circuitry 80 stores a plurality of reception delay patterns with different focus depths, a plurality of transmission delay patterns, a plurality of shear wave generation transmission delay patterns, control programs for the ultrasonic diagnostic apparatus 1, a diagnostic program, various types of data groups such as transmission/reception conditions, diagnostic information (patient IDs, findings by doctors, and the like), the reception signals generated by the reception circuitry, the B-mode data generated by the B-mode processing circuitry 40, the Doppler data generated by the Doppler processing circuitry 50, first and second displacement data at each position in a predetermined region, body motion displacement data, shear wave propagation data, a propagation time hue correspondence table, B-mode images, average velocity images, variance images, power images, shear wave propagation images, an algorithm (to be referred to as a shear wave propagation image generation algorithm hereinafter) concerning the generation of shear wave propagation images, and the like. In addition, the storage circuitry 80 includes a memory (not represented) and stores data (to be referred to as image data hereinafter) corresponding to generated ultrasonic images (B-mode images, average velocity images, variance images, power images, and shear wave propagation images). Image data stored in the memory is read out in accordance with an instruction from the operator via the input interface circuitry 5 (to be described later). This memory is, for example, a memory which stores ultrasonic images corresponding to a plurality of frames immediately before freezing. Continuously displaying (cine displaying) the images stored in this cine memory can display a moving ultrasonic image on the display circuitry 4 (to be described later). The host computer 10 executes the above programs stored in the storage circuitry 80. The host computer 10 executes write/read of the above data and the like to/from the memory.

The interface circuitry 90 is an interface concerning the input interface circuitry 5 and the network 6. Data such as the ultrasonic images, the analysis results, and the like, which are obtained by the apparatus main body 3, can be transferred to other apparatuses via the interface circuitry 90 and the network 6. Note that the interface circuitry 90 can also download, via the network 6, medical images concerning objects acquired by other medical image diagnostic apparatuses.

The display circuitry 4 displays a B-mode image, an ultrasonic image such as a Doppler image, a shear wave propagation image, a superimposed image, or the like based on an output from the image combining circuitry 70. Note that the display circuitry 4 may execute adjustment such as brightness correction, contrast correction, dynamic range correction, and $\gamma$ correction and color mapping with respect to a displayed image.

The input interface circuitry 5 is connected to the interface circuitry 90 to input, to the apparatus main body 3, various types of instructions, commands, information, selections, and settings from an operator such as a doctor. The input interface circuitry 5 includes input devices such as a trackball, switch buttons, a mouse, and a keyboard. These input devices detect the coordinates of the cursor displayed on the display screen and output the detected coordinates to the host computer 10. Note that the input device may be a touch command screen provided to cover the display screen. In this case, the input interface circuitry 5 detects touched and designated coordinates by a coordinate reading principle such as an electromagnetic induction scheme, magnetostriction scheme, or a pressure-sensitive scheme, and outputs the detected coordinates to the host computer 10. When, for example, the operator operates the end button or freeze button of the input interface circuitry 5, the ultrasonic transmission/reception is terminated, and the apparatus main body 3 is set in a pause state.

In addition, the input interface circuitry 5 accepts an ROI (Region of Interest) input by the operator or a predetermined region on which the operator focuses attention. The input interface circuitry 5 accepts the input of the mode selected by the operator.

Figure 2:
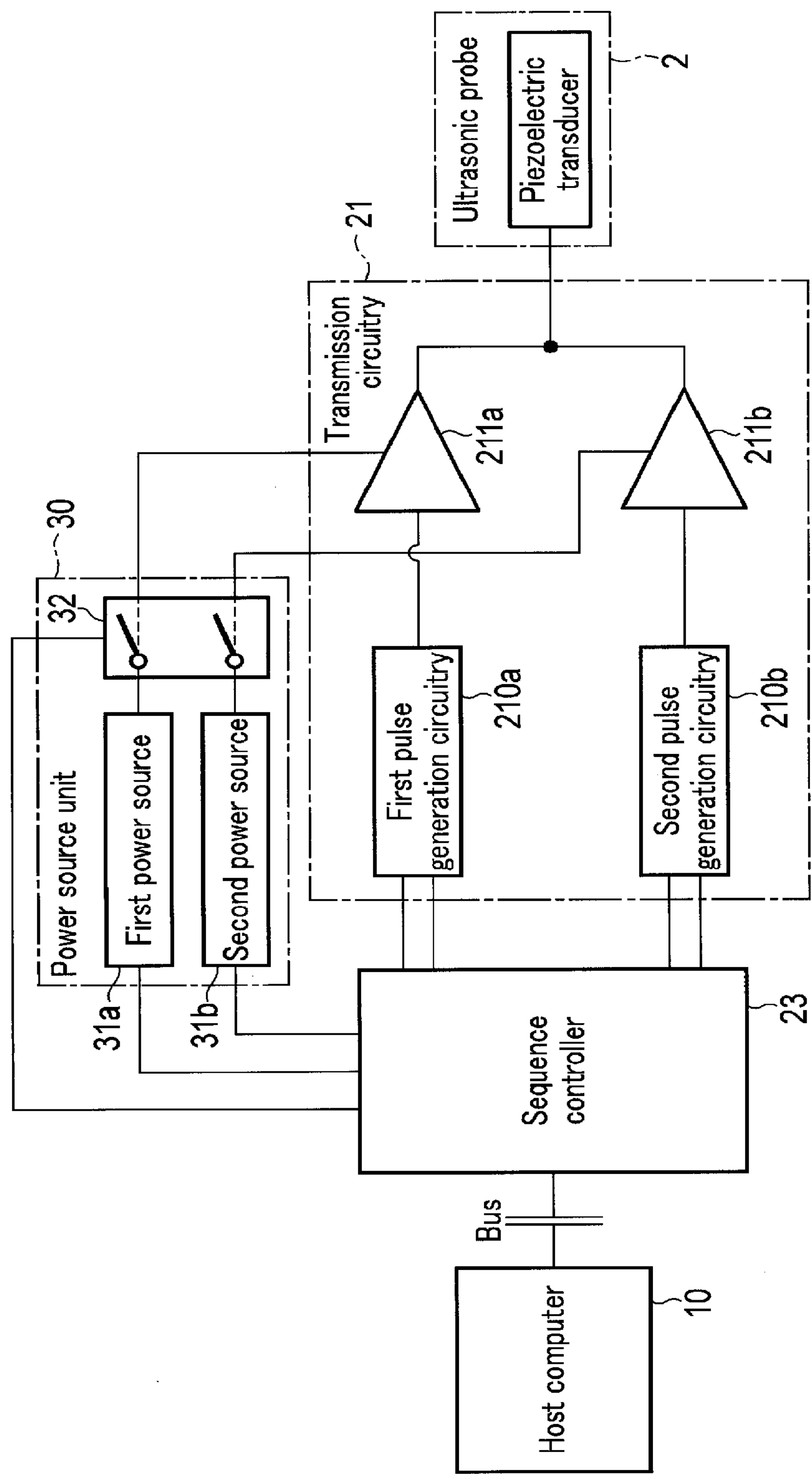
FIG. 2 is a block diagram representing an example of transmission circuitry according to the first embodiment.

FIG. 2 is a block diagram representing an example of transmission circuitry 21 according to the first embodiment. FIG. 2 represents the ultrasonic probe 2, the host computer 10, a sequence controller 23, the power source unit 30 (power sources (the first power source 31*a* and the second power source 31*b*) and an electronic switch 32) in association with the transmission circuitry 21. The transmission circuitry 21 includes pulse generation circuitry (first pulse generation circuitry 210*a* and second pulse generation circuitry 210*b*) and pulsers (a first pulser 211*a* and a second pulser 211*b*). Although FIG. 2 represents the single transmission circuitry 21, a plurality of transmission circuits 21 are provided in practice. A general arrangement is configured to selectively switch between a plurality of transducers connected to one transmission circuitry.

The first power source 31*a* is connected to a first pulser 211*a* to apply the voltage required for the generation of a driving pulse string to the first pulser 211*a*. Likewise, the second power source 31*b* is connected to a second pulser 211*b* to apply the voltage required for the generation of a driving pulse string to the second pulser 211*b*. The electronic switch 32 switches between executing and stopping the application of a voltage from the first power source 31*a* or the second power source 31*b*.

Note that, for example, a mechanical switch may be provided in place of the electronic switch 32. FIG. 2 separately represents the electronic switch 32 and the power sources. In practice, however, the electronic switch 32 may be designed separately from the power sources or may be designed to be incorporated in the power source circuitry.

The sequence controller 23 is connected to the transmission circuitry 21 and the power source unit 30 to control the operation of the transmission circuitry 21 and the operation of the power source unit 30 with high time resolutions on the order of several ten μs to several hundred μs. The sequence controller 23 transmits clock signals (clocks or clock pulses) based on the time resolutions to the first pulse generation circuitry 210*a* and the second pulse generation circuitry 210*b*. The first pulse generation circuitry 210*a* and the second pulse generation circuitry 210*b* generate excitation pulse strings by phase controllably frequency-dividing clock signals from the sequence controller 23. The first pulse generation circuitry 210*a* transmits the excitation pulse string to the first pulser 211*a* connected to the first pulse generation circuitry 210*a*. Likewise, the second pulse generation circuitry 210*b* transmits the excitation pulse string to the second pulser 211*b* connected to the second pulse generation circuitry 210*b*.

The first pulser 211*a* and the second pulser 211*b* are respectively connected to the first power source 31*a* and the second power source 31*b* via the electronic switch 32.

That is, these pulsers form two signal systems, each including one power source and one pulser. The first pulser 211*a* generates a driving pulse string by amplifying an excitation pulse string in accordance with an applied voltage from the first power source 31*a*, and transmits the driving pulse string to the piezoelectric transducers of the ultrasonic probe 2. The first pulser 211*a* transmits no signal when an applied voltage from the first power source 31*a* is stopped by the electronic switch 32. Likewise, the second pulser 211*b* generates a driving pulse string by amplifying an excitation pulse string in accordance with an applied voltage from the second power source 31*b*, and transmits the driving pulse string to the piezoelectric transducers of the ultrasonic probe 2. The first second pulser 211*b* transmits no signal when an applied voltage from the second power source 31*b* is stopped by the electronic switch 32.

Note that in order to avoid redundancy, refer to the description made with reference to FIG. 1 for the operations of the ultrasonic probe 2 and the host computer 10 in FIG. 2.

The power switching function of the ultrasonic diagnostic apparatus 1 according to this embodiment will be described next.

The sequence controller 23 exclusively (alternatively or alternately) selects a power source (the first power source 31*a* or the second power source 31*b*) to apply a voltage to a pulser (the first pulser 211*a* or the second pulser 211*b*) by switching the electronic switch 32 in a transmission mode period (e.g., a period during which push pulses are transmitted to generate shear waves from an object) (power source switching function). This is merely an example and is not exhaustive. The power source (e.g., the first power source 31*a*) selected by the sequence controller 23 applies a voltage to a pulser (e.g., the first pulser 211*a*) in a selected period. The power source (e.g., the second power source 31*b*) which is not selected by the sequence controller 23 applies no voltage to a pulser (e.g., the second pulser 211*b*) in a period during which the power source is not selected.

The sequence controller 23 may switch the electronic switch 32 at the time intervals set in advance by a doctor or the like or may switch the electronic switch 32 for each pulse output count set in advance by an operator such as a doctor (open loop control).

A power source which is not selected will be referred to as an inactive power source. The sequence controller 23 executes control to change the value of the open voltage of an inactive power source.

FIG. 3 represents timing charts representing a transmission pulse sequence using the power source switching function in shear wave elastography according to the first embodiment. Assume that the transmission pulse sequence in this shear wave elastography is the sequence constituted by a push pulse period, a tracking period, and a B-mode image generation period in the order named.

FIG. 3 represents four timing charts (a) to (d) in order from the top. In FIG. 3, (a) represents a temporal change in the open voltage of the first power source 31*a*. In FIG. 3, (b) represents a temporal change in the open voltage of the second power source 31*b*. In FIG. 3, (c) represents a temporal change of a power source selected by the sequence controller 23. That is, "1" in (c) in FIG. 3 represents a state in which the first power source 31*a* is selected. In FIG. 3, "2" in (c) represents a state in which the second power source 31*b* is selected. In FIG. 3, (d) represents a temporal change of a driving pulse string (peak value) transmitted from one of the pulsers to the piezoelectric transducers of the ultrasonic probe 2.

In FIG. 3, $V_0$, $V_1$, $V'_0$, and $V_2$ in (a), (b), and (d) respectively represent voltage values. In addition, $T_0$ to $T_{10}$ in (c) in FIG. 3 respectively represent the times at which a power source is selected (the times at which a selected power source is switched) in the order named.

The sequence controller 23 exclusively selects a power source from which the ultrasonic diagnostic apparatus 1 transmits an applied voltage to a pulser in a push pulse period as a transmission mode. That is, the sequence controller 23 exclusively switches a power source to be selected.

For example, the sequence controller 23 selects the first power source 31*a* at time $T_0$ (the start time of a push pulse period). The sequence controller 23 switches a power source to be selected from the first power source 31*a* to the second power source 31*b* at time $T_1$ (e.g., 150 μs after time $T_0$). The sequence controller 23 switches a power source to be selected from the second power source 31*b* to the first power source 31*a* at time $T_2$ (e.g., 150 μs after time $T_1$). The sequence controller 23 switches a power source to be selected from the first power source 31*a* to the second power source 31*b* at time $T_3$ (e.g., 150 μs after time $T_2$). The sequence controller 23 switches a power source to be selected from the second power source 31*b* to the first power source 31*a* at time $T_4$ (e.g., 150 μs after time $T_3$). The sequence controller 23 switches a power source to be selected from the first power source 31*a* to the second power source 31*b* at time $T_5$ (e.g., 150 μs after time $T_4$). In this manner, in a push pulse period, the first power source 31*a* or the second power source 31*b* is exclusively selected. The ultrasonic probe 2 transmits a push pulse (a strong ultrasonic pulse for the generation of a shear wave from the interior of the object) in a push pulse period in response to a driving pulse string whose peak value is a maximum value $V_0$ transmitted from a pulser (the first pulser 211*a* or the second pulser 211*b*) corresponding to a power source to be selected (the first power source 31*a* or the second power source 31*b*). The ultrasonic probe 2 may transmit push pulses to, for example, a plurality of portions in the object in a push pulse period (a push pulse transmission time at one portion is, for example, 900 μs).

In the period from time $T_5$ to time $T_6$, the first power source 31*a* is inactive. The sequence controller executes control to change the open voltage of the inactive first power source 31*a* from $V_0$ (e.g., 100 V) to $V_1$ (e.g., 130 V).

The sequence controller 23 switches a power source to be selected from the second power source 31*b* to the first power source 31*a* at time $T_6$ (the start time of a tracking period). The ultrasonic probe 2 transmits a tracking pulse (an ultrasonic pulse for the measurement of the propagation velocity of a shear wave generated from the interior of the object) in a tracking pulse transmission period (e.g., 700 μs) in response to a driving pulse string whose peak value (its maximum value) is $V_1$ transmitted from the first pulser 211*a*.

In the period from time $T_6$ to time $T_7$, the second power source 31*b* is inactive. The sequence controller executes control to change the open voltage of the inactive second power source 31*b* from $V_0$ (e.g., 100 V) to $V_2$ (e.g., 150 V).

The sequence controller 23 switches a power source to be selected from the first power source 31*a* to the second power source 31*b* at time $T_7$ (the start time of a B-mode image generation period). The ultrasonic probe 2 transmits a B-mode pulse (an ultrasonic pulse for the generation of a B-mode image) in a B-mode image generation period (e.g., 500 μs) in response to a driving pulse string whose peak value (its maximum value) is $V_2$ transmitted from the second pulser 211*b*. In the period from time $T_7$ to time $T_8$, the sequence controller 23 decides $V'_0$ as a voltage to be applied in a push pulse period in the next ultrasonic transmission/reception sequence based on an obtained shear wave analysis result or B-mode image. That is, the sequence controller 23 executes control to change the open voltage of the inactive first power source 31*a* from $V_1$ (e.g., 130 V) to $V'_0$ (e.g., 80 V). Subsequently, in the period from time $T_8$ to time $T_9$, the sequence controller 23 executes control to change the open voltage of the inactive second power source 31*b* from $V_2$ (e.g., 150 V) to $V'_0$ (e.g., 80 V). The operation associated with the above sequence of an ultrasonic transmission/reception sequence (e.g., 1 sec) is executed a plurality of times.

It is possible to implement shear wave elastography of diagnosing hardness by using the ultrasonic diagnostic apparatus 1 according to the first embodiment described above.

(First Modification)

In the ultrasonic diagnostic apparatus 1 according to the first embodiment described above, one pulse generation circuitry (e.g., the first pulse generation circuitry 210*a*) is connected to one pulser (e.g., the first pulser 211*a*). In the above case, however, since the sequence controller 23 exclusively selects a power source, a plurality of pulsers do not simultaneously output pulses. That is, as a modification, one pulse generation circuitry may be connected to each of a plurality of pulsers via a logic gate 212.

Figure 4:
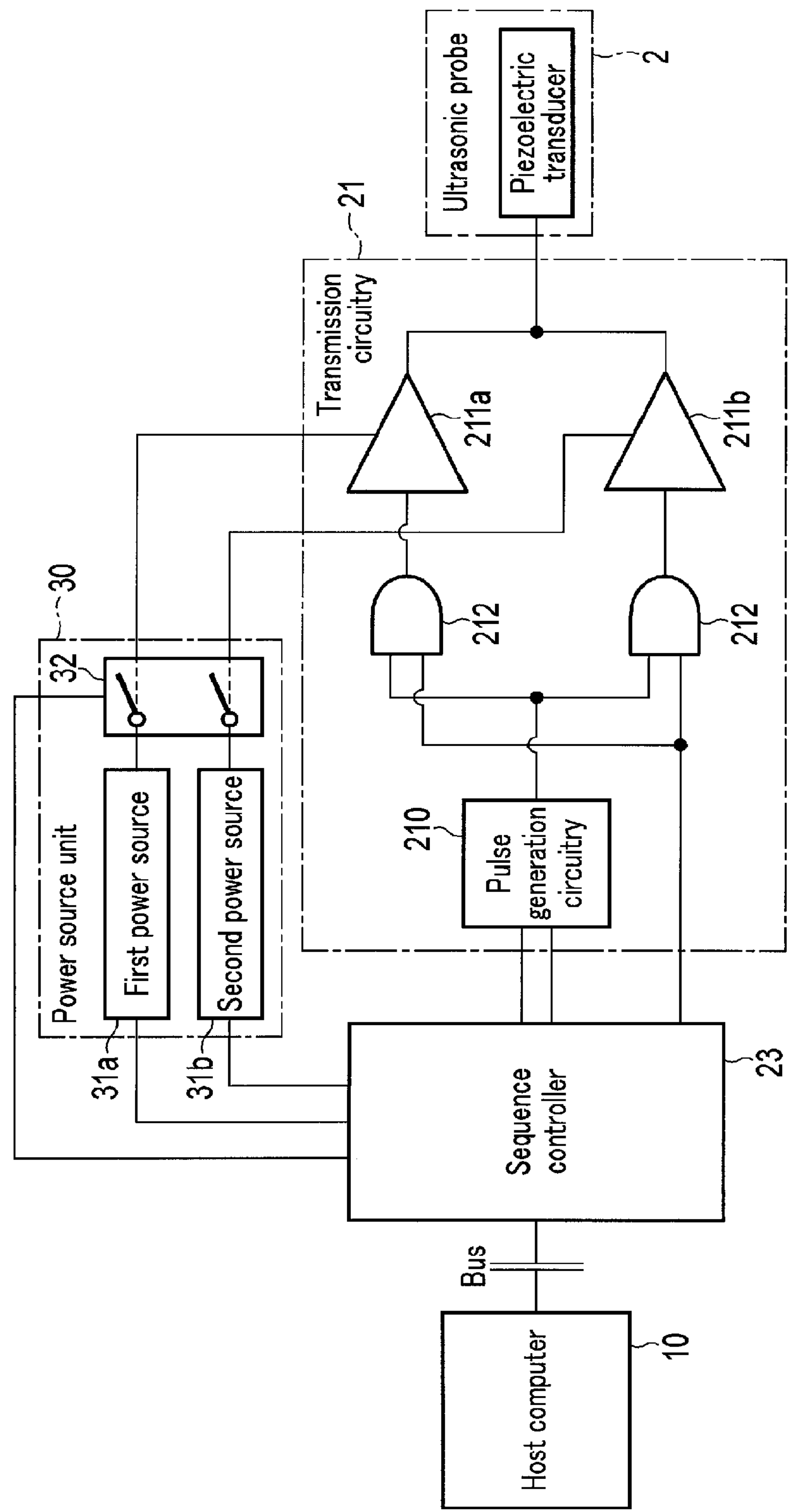
FIG. 4 is a block diagram representing a modification of transmission circuitry using logic gates according to the first embodiment.

FIG. 4 is an example of a block diagram of a transmission circuitry according to this modification of the first embodiment. The transmission circuitry 21 includes one pulse generation circuitry (a pulse generation circuitry 210), pulsers (the first pulser 211*a* and the second pulser 211*b*), and the logic gates 212 corresponding to the respective pulsers. The logic gates 212 corresponding to the respective pulsers (the first pulser 211*a* and the second pulser 211*b*) are connected to the sequence controller 23. The sequence controller 23 transmits the excitation pulse string generated by the pulse generation circuitry 210 to the pulser (e.g., the first pulser 211*a*) corresponding to the selected power source via the logic gate 212 based on the selected power source (e.g., the first power source 31*a*). The first modification can also obtain the same effects as those obtained by the first embodiment.

(Second Modification)

In the ultrasonic diagnostic apparatus 1 according to the first embodiment including the first modification, one pulser (e.g., the first pulser 211*a*) is connected to one power source (e.g., the first power source 31*a*). This arrangement will be referred to as a single power source connected pulser. However, the number of pulsers may not correspond to the number of power sources in some case. For example, one pulser (e.g., the first pulser 211*a*) may be connected to a plurality of power sources (e.g., the first power source 31*a* and the second power source 31*b*). This arrangement will be referred to as a multiple power source connected pulser. The ultrasonic diagnostic apparatus 1 may include one multiple power source connected pulser. Alternatively, the ultrasonic diagnostic apparatus 1 may include both a single power source connected pulser and a multiple power source connected pulser. In this case as well, the sequence controller 23 exclusively switches between the power sources. The second modification can also obtain the same effects as those described in the first embodiment.

(Third Modification)

The ultrasonic diagnostic apparatus 1 may include three or more power sources. The ultrasonic diagnostic apparatus 1 may include three or more pulsers. In this case as well, the sequence controller 23 exclusively switches between power sources. The third modification can also obtain the same effects as those obtained by the first embodiment which will be described later.

(Fourth Modification)

The ultrasonic diagnostic apparatus 1 exclusively switches between power sources. However, the technique of exclusively switching is merely an example and is not exhaustive. For example, a plurality of power sources (including some or all of the power sources) may be switched so as to be simultaneously used. For example, an overall applied voltage droop may be suppressed by lowering the voltage values of the respective power sources. Alternatively, while a plurality of power sources are simultaneously used, one power source may be selected as the main power source, and the remaining power sources may be used as auxiliary power sources. In such a case, the auxiliary power sources preferably apply voltages with lower voltage values than the voltage value of the main power source. In addition, exclusive switching and switching for simultaneous use may be performed within one sequence. The fourth modification can also obtain the same effects as those of the first embodiment which will be described later.

(Fifth Modification)

The power source unit 30 of the ultrasonic diagnostic apparatus 1 includes a plurality of power supplies. Therefore, some or all of the plurality of power sources in the power source unit 30 may be implemented by being replaced with capacitors or storage batteries typified by lead storage batteries, nickel cadmium batteries, and lithium ion batteries. That is, voltages may be applied to pulsers by using charge accumulated in the capacitors or power stored in the storage batteries. The fifth modification can also obtain the same effects as those obtained by the first embodiment which will be described later.

The ultrasonic diagnostic apparatus 1 according to the first embodiment can obtain the following effects.

As described above, for example, the sequence controller 23 exclusively selects a power source to apply a voltage to a pulser by switching the electronic switch 32. This shortens the period during which one power source is used, thereby reducing a droop in applied voltage. In addition, reducing the capacitance of a decoupling capacitor provided to reduce a droop can achieve downsizing of a power source. In addition, it is possible to transmit driving pulse strings with stable push pulse outputs to the ultrasonic probe 2 regardless of transmission conditions for push pulses output from the ultrasonic probe 2. Therefore, the ultrasonic probe 2 may either a general one-dimensional array probe or a linear array probe which implements a wide field of view by connecting multiple arrays of piezoelectric transducers by switching them using a built-in high-pressure switch. Alternatively, the ultrasonic probe 2 may be a 1.25-dimensional probe or 1.5-dimensional probe which is designed to also divide piezoelectric transducers in the lens direction and connect them upon aperture switching.

As described above, a characteristic feature of this embodiment is that an inactive power source applies no voltage to a pulser. For this reason, the inactive power source can restore the applied voltage which has drooped at the time of an operation to the open voltage. That is, it is possible to reduce the influence of a droop in voltage at the time of the transmission of relatively strong ultrasonic waves such as push pulses.

The ultrasonic diagnostic apparatus 1 includes a plurality of power sources (e.g., two power sources). The plurality of power sources are exclusively selected. That is, the power value required for each of the plurality of power sources can be kept low. For this reason, it is possible to achieve downsizing and a reduction in cost of the circuitry constituted by power sources. In addition, the amount of heat generated is suppressed as compared that in related art, and hence cooling is facilitated.

As described above, the sequence controller 23 can execute control to change the value of the open voltage of an inactive power source. For this reason, the ultrasonic diagnostic apparatus 1 can implement shear wave measurement with higher sensitivity by changing the value of the open voltage of an inactive power source at the time of transition from a push pulse period to a tracking pulse period in, for example, shear wave elastography. Likewise, the ultrasonic diagnostic apparatus 1 can generate a B-mode image with higher sensitivity by changing the value of the open voltage of an inactive power source at the time of transition from a tracking pulse period to a B-mode pulse period in, for example, shear wave elastography.

(Comparison with Prior Art)

FIG. 5 is a block diagram representing an example of transmission circuitry in a conventional ultrasonic diagnostic apparatus. A conventional ultrasonic diagnostic apparatus 1 does not have the power source switching function of this embodiment. In addition, the conventional ultrasonic diagnostic apparatus 1 cannot change the value of the open voltage of an inactive power source.

Figure 6:
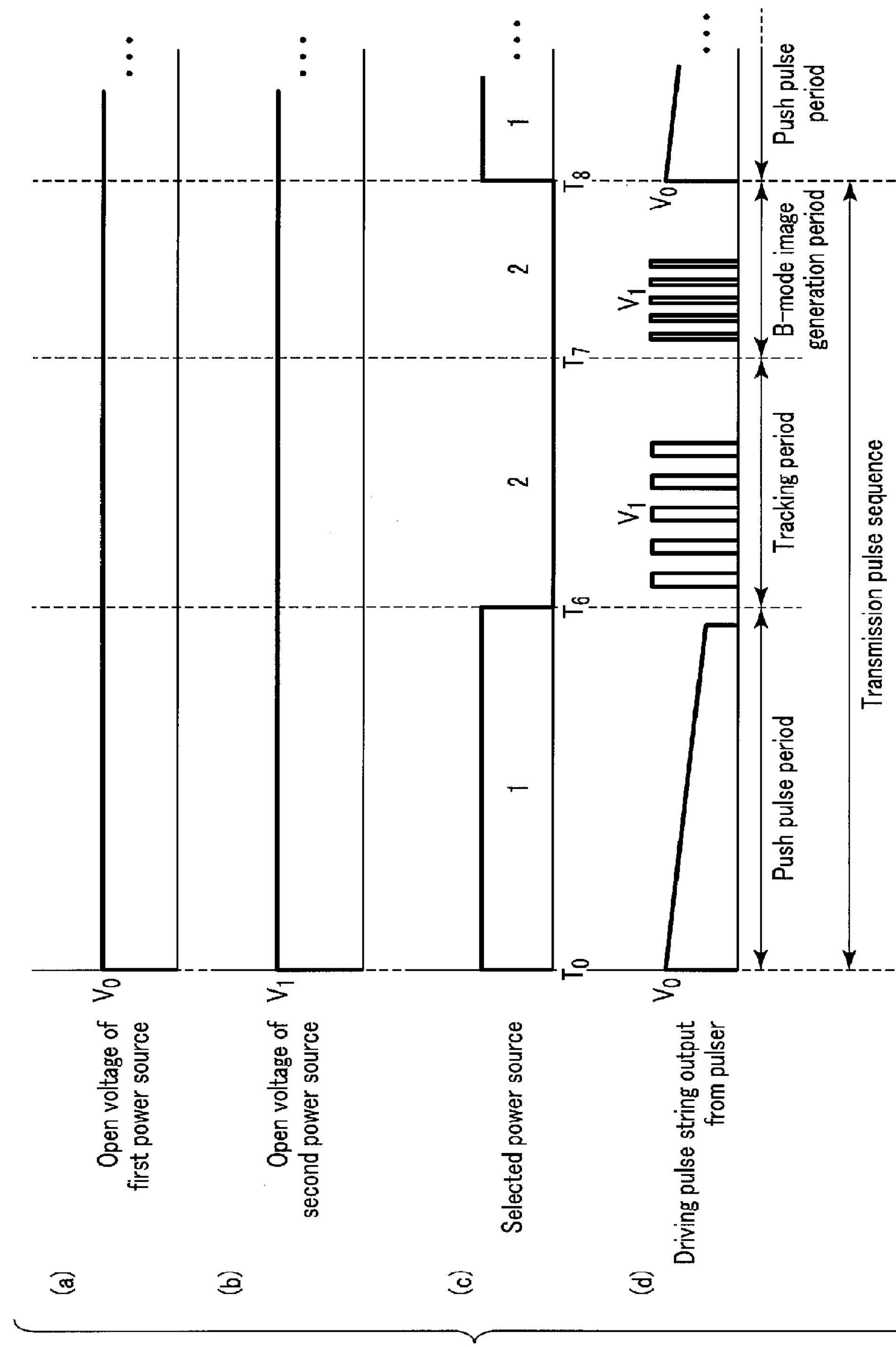
FIG. 6 represents an example of timing charts representing an ultrasonic transmission/reception sequence in shear wave elastography using a conventional ultrasonic diagnostic apparatus.

FIG. 6 represents an example of timing charts representing a transmission pulse sequence in shear wave elastography using the conventional ultrasonic diagnostic apparatus. FIG. 6 represents four timing charts (a) to (d) in order from the top. In FIG. 6, (a) represents a temporal change in the open voltage of a first power source 31*a*. In FIG. 6, (b) represents a temporal change in the open voltage of a second power source 31*b*. In FIG. 6, (c) represents a temporal change of a power source selected by a sequence controller 23. That is, "1" in (c) in FIG. 6 represents a state in which the first power source 31*a* is selected. In FIG. 6, "2" in (c) represents a state in which the second power source 31*b* is selected. In FIG. 6, (d) represents a temporal change of a driving pulse string (peak value) transmitted from one of the pulsers to the piezoelectric transducers of an ultrasonic probe 2.

$V_0$ and $V_1$ in (a), (b), and (d) in FIG. 6 respectively correspond to $V_0$ and $V_1$ in (c) in FIG. 3, and respectively indicate voltage values. In addition, $T_0$ and $T_6$ to $T_8$ in (c) in FIG. 6 respectively correspond to $T_0$ and $T_6$ to $T_8$ in (c) in FIG. 3, and represent the times at which a power source is selected (the times at which a selected power source is switched).

The conventional ultrasonic diagnostic apparatus uses one power source (the first power source 31*a* in this case) in a push pulse period. For this reason, the influence of a droop in applied voltage becomes noticeable (see the comparison between (d) in FIG. 3 and (d) in FIG. 6). In addition, the capacitance of a decoupling capacitor provided to reduce a droop increases, resulting in an increase in the size of a power source. Furthermore, the amount of heat generated becomes larger than that in this embodiment. This makes it difficult to perform cooling.

In addition, since a conventional power source has a fixed open voltage, the conventional ultrasonic diagnostic apparatus 1 is lower in shear wave measurement sensitivity and B-mode image generation sensitivity than this embodiment (see the comparison between (a) and (b) in FIG. 3 and (a) and (b) in FIG. 6).

(Second Embodiment)

In the first embodiment, the sequence controller 23 executes the power switching function at predetermined time intervals or in response to a predetermined pulse output count as a trigger (open loop control). On the other hand, in the second embodiment, a sequence controller 23 executes the power switching function under the feedback control using a comparator.

FIG. 7 is a block diagram representing an example of a transmission circuitry 21 according to the second embodiment. The same reference numerals denote the same constituent elements as those in the first embodiment, and a repetitive description will be omitted. In association with the transmission circuitry 21, FIG. 7 also represents an ultrasonic probe 2, a host computer 10, the sequence controller 23, and a power source unit 30 (power sources (a first power source 31*a* and a second power source 31*b*) and an electronic switch 32). The transmission circuitry 21 includes a pulse generation circuitry 210, pulsers (a first pulser 211*a* and a second pulser 211*b*), logic gates 212 corresponding to the respective pulsers, and comparators (a first comparator 213*a* and a second comparator 213*b*) corresponding to the respective power sources. In addition, an ultrasonic diagnostic apparatus 1 according to the second embodiment has the above power source switching function.

The first comparator 213*a* compares the applied voltage transmitted from the first power source 31*a* to the first pulser 211*a* and the first constant voltage (the monitoring voltage of the first power source) output from the host computer 10 (monitoring means). For example, the monitoring voltage of the first power source may be set to, for example, 90% of the open voltage of the first power source 31*a*, as a threshold. The first comparator 213*a* transmits two different voltage values (i.e., 1-bit computation representing 0 or 1) to the sequence controller 23 based on the comparison result. When, for example, the sequence controller 23 has selected the first power source 31*a*, the sequence controller 23 selects the second power source 31*b* via the electronic switch 32 in response to a moment when the applied voltage becomes lower than the threshold, i.e., the voltage value representing 0 switches to the voltage value representing 1 (or the voltage value representing 1 switches to the voltage value representing 0) as a trigger.

Likewise, a second comparator 213*b* compares the applied voltage transmitted from the second power source 31*b* to the second pulser 211*b* and the second constant voltage (the monitoring voltage of the second power source) output from the host computer 10. For example, the monitoring voltage of the second power source may be set to, for example, 90% of the open voltage of the second power source 31*b*, as a threshold. The second comparator 213*b* transmits two different voltage values (i.e., 1-bit computation representing 0 or 1) to the sequence controller 23 based on the comparison result. When, for example, the sequence controller 23 has selected the second power source 31*b*, the sequence controller 23 selects the first power source 31*a* via the electronic switch 32 in response to a moment when the applied voltage becomes lower than the threshold, i.e., the voltage value representing 0 switches to the voltage value representing 1 (or the voltage value representing 1 switches to the voltage value representing 0) as a trigger.

The ultrasonic diagnostic apparatus 1 according to the second embodiment can obtain the following effects.

As described above, for example, the sequence controller 23 exclusively selects a power source to apply a voltage to a pulser by switching the electronic switch 32. This shortens the period during which one power source is used, and can reduce a droop in applied voltage. In addition, reducing the capacitance of a decoupling capacitor provided to reduce a droop can achieve downsizing of the power source. In addition, it is possible to transmit a stable driving pulse string for stabilizing a push pulse output regardless of the transmission conditions for the push pulse output from the ultrasonic probe 2. Therefore, the ultrasonic probe 2 may either a general one-dimensional array probe or a linear array probe which implements a wide field of view by connecting multiple arrays of piezoelectric transducers by switching them using a built-in high-pressure switch. Alternatively, the ultrasonic probe 2 may be a 1.25-dimensional probe or 1.5-dimensional probe which is designed to also divide piezoelectric transducers in the lens direction and connect them upon aperture switching.

As described above, a characteristic feature of this embodiment is that an inactive power source applies no voltage to a pulser. For this reason, the inactive power source can restore the applied voltage which has drooped at the time of an operation to the open voltage. That is, it is possible to reduce the influence of a droop in voltage at the time of the transmission of relatively strong ultrasonic waves such as push pulses.

The ultrasonic diagnostic apparatus 1 includes a plurality of power sources (e.g., two power sources). The plurality of power sources are exclusively selected. That is, the power value required for each of the plurality of power sources can be kept low. For this reason, it is possible to achieve downsizing and a reduction in cost of the circuitry constituted by power sources. In addition, the amount of heat generated is suppressed as compared with that in related art, and hence cooling is facilitated.

As described above, the sequence controller 23 can execute control to change the value of the open voltage of an inactive power source. For this reason, the ultrasonic diagnostic apparatus 1 can implement shear wave measurement with higher sensitivity by changing the value of the open voltage of an inactive power source at the time of transition from a push pulse period to a tracking pulse period in, for example, shear wave elastography. Likewise, the ultrasonic diagnostic apparatus 1 can generate a B-mode image with higher sensitivity by changing the value of the open voltage of an inactive power source at the time of transition from a tracking pulse period to a B-mode pulse period in, for example, shear wave elastography.

Note that a plurality of units or apparatuses according to the present embodiment may be implemented by processors or processing circuitry. The processing circuitry may be constituted of a singular set of circuitry such as a CPU, plural sets of circuitry corresponding to each of the units, or the combination thereof.

Furthermore, the word "processor" or "processing circuitry" used in the above description means circuitry such as a CPU (Central Processing Unit), a GPU (Graphics Processing Unit), an ASIC (Application Specific Integrated Circuit), a programmable logic device (e.g., an SPLD (Simple Programmable Logic Device), a CPLD (Complex Programmable Logic Device), or an FPGA (Field Programmable Gate Array)), or the like. The processor implements functions by reading out programs stored in the storage circuit and executing the programs. Note that it is possible to directly incorporate programs in the circuit of the processor instead of storing the programs in the storage circuit. In this case, the processor implements functions by reading out programs incorporated in the circuit and executing the programs.

Note that each processor in each embodiment described above may be formed as one processor by combining a plurality of independent circuits to implement functions as well as being formed as a single circuit for each processor. In addition, a plurality of constituent elements in each embodiment described above may be integrated into one processor to implement its function.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

The invention claimed is:

1. An ultrasonic diagnostic apparatus, comprising:

an ultrasonic probe including a plurality of piezoelectric transducers, and configured to generate ultrasonic waves in response to supplied driving pulse signals;

at least one pulser configured to output a driving pulse signal to at least one of the plurality of piezoelectric transducers;

a plurality of power supplies implemented by circuitry and associated with the at least one pulser to apply voltages to the at least one pulser for generation of the driving pulse signal; and a controller implemented by circuitry, configured to alternately select, at predetermined timing, application of the voltages from the plurality of power supplies in a push pulse transmission period in shear wave elastography during which push pulses are transmitted by the ultrasonic probe so as to prevent voltage droop in the voltages applied to the at least one pulser, wherein one of more power supplies of the plurality of power supplies that are not selected for the application of the voltages apply no voltage to the at least one pulser.

2. An ultrasonic diagnostic apparatus, comprising:

an ultrasonic probe including a plurality of piezoelectric transducers, and configured to generate ultrasonic waves in response to supplied driving pulse signals;

at least one pulser configured to output a driving pulse signal to at least one of the plurality of piezoelectric transducers;

a plurality of power supplies implemented by circuitry and associated with the at least one pulser to apply voltages to the at least one pulser for generation of the driving pulse signal; and a controller implemented by circuitry, configured to alternately select, at predetermined timing, application of the voltages from the plurality of power supplies in an ultrasonic transmission period during drug delivery to control an internal distribution of a drug in an object by using breakage of a capsule of the drug with ultrasonic waves from the ultrasonic probe so as to prevent voltage droop in the voltages applied to the at least one pulser, one of more power supplies of the plurality of power supplies that are not selected for the application of the voltages apply no voltage to the at least one puller.

3. The apparatus according to the claim 1, wherein the controller is further configured to alternately select application of the voltages from the power supplies at predetermined time intervals.

4. The apparatus according to the claim 1, wherein the controller is further configured to alternately select application of the voltages from the power supplies for each of predetermined pulse output counts.

5. The apparatus according to the claim 1, further comprising a monitoring unit implemented by circuitry, configured to monitor the applied voltage, wherein the controller is further configured to alternately select application of the voltages from the power supplies every time the applied voltage becomes lower than a predetermined threshold.

6. The apparatus according to the claim 1, wherein the controller is further configured to change an open voltage of an inactive power supply.

7. The apparatus according to the claim 1, wherein the plurality of power supplies each comprise at least one of a power source, a storage battery, and a capacitor.

8. The apparatus according to the claim 2, wherein the controller is further configured to alternately select application of the voltages from the power supplies at predetermined time intervals.

9. The apparatus according to the claim 2, wherein the controller is further configured to alternately select application of the voltages from the power supplies for each of predetermined pulse output counts.

10. The apparatus according to the claim 2, further comprising a monitoring unit implemented by circuitry, configured to monitor the applied voltage, wherein the controller is further configured to alternately select application of the voltages from the power supplies every time the applied voltage becomes lower than a predetermined threshold.

11. The apparatus according to the claim 2, wherein the controller is further configured to change an open voltage of an inactive power supply.

12. The apparatus according to the claim 2, wherein the plurality of power supplies each comprise at least one of a power source, a storage battery, and a capacitor.

* * * * *